United States Patent
Ormsby et al.

(10) Patent No.: US 8,679,106 B2
(45) Date of Patent: Mar. 25, 2014

(54) ANGIOPLASTY AND TISSUE ABLATION APPARATUS AND METHOD

(75) Inventors: Theodore C. Ormsby, Escondido, CA (US); George Leung, San Diego, CA (US); Gwo Jenn Shen, Carlsbad, CA (US)

(73) Assignee: Medwaves, Inc., San Diego, CA (US)

( * ) Notice: Subject to any disclaimer, the term of this patent is extended or adjusted under 35 U.S.C. 154(b) by 1381 days.

(21) Appl. No.: 12/166,159

(22) Filed: Jul. 1, 2008

(65) Prior Publication Data

US 2010/0004650 A1   Jan. 7, 2010

(51) Int. Cl.
 *A61B 18/14* (2006.01)
(52) U.S. Cl.
 USPC .............................. 606/33; 606/41
(58) Field of Classification Search
 USPC ............. 606/7, 28, 33, 40, 47; 600/115, 372, 600/373, 381; 607/102, 156
 See application file for complete search history.

(56) References Cited

U.S. PATENT DOCUMENTS

| | | | |
|---|---|---|---|
| 3,309,455 A | 3/1967 | Mildner | |
| 4,271,848 A | 6/1981 | Turner et al. | |
| 4,408,089 A | 10/1983 | Nixon | |
| 4,583,556 A | 4/1986 | Hines et al. | |
| 4,776,086 A | 10/1988 | Kasevich | |
| 5,035,694 A * | 7/1991 | Kasprzyk et al. | 606/27 |
| 5,057,106 A * | 10/1991 | Kasevich et al. | 606/33 |
| 5,150,717 A * | 9/1992 | Rosen et al. | 607/156 |
| 5,275,597 A * | 1/1994 | Higgins et al. | 606/33 |
| 5,370,644 A | 12/1994 | Langberg | |
| 5,370,677 A | 12/1994 | Rudie et al. | |
| 5,372,603 A * | 12/1994 | Acker et al. | 606/194 |
| 5,496,271 A * | 3/1996 | Burton et al. | 607/27 |
| 5,500,012 A | 3/1996 | Brucker et al. | |
| 5,545,193 A | 8/1996 | Fleischman et al. | |
| 5,656,029 A | 8/1997 | Miran et al. | |
| 5,656,796 A | 8/1997 | Marinos et al. | |
| 5,683,382 A | 11/1997 | Lenihan et al. | |
| 5,702,433 A | 12/1997 | Taylor et al. | |

(Continued)

FOREIGN PATENT DOCUMENTS

EP     1055399 A1    11/2000
WO     92/04934      4/1992

(Continued)

OTHER PUBLICATIONS

Office Action dated from U.S. Appl. No. 11/781,467 dated Jun. 23, 2011.

(Continued)

*Primary Examiner* — Michael Peffley
*Assistant Examiner* — Thomas Giuliani
(74) *Attorney, Agent, or Firm* — Cesari and McKenna, LLP (57) ABSTRACT

A coaxial cable apparatus which transmits radio frequency (RF) energy for the ablation of biological tissues has inner and outer coaxial conductors extending substantially the entire length of the cable from a proximal end portion to a distal end portion. An RF antenna is disposed at the distal end portion of the cable and transmits RF energy for ablation of a tissue region to be treated. An angioplasty balloon is disposed over the RF antenna and communicates with a fluid supply and extraction passageway extending through the cable to allow the balloon to be inflated for an angioplasty procedure including tissue ablation, and to be deflated after the procedure is complete.

16 Claims, 7 Drawing Sheets

(56) References Cited

U.S. PATENT DOCUMENTS

| | | |
|---|---|---|
| 5,738,683 A | 4/1998 | Osypka |
| 5,741,249 A | 4/1998 | Moss et al. |
| 5,755,754 A | 5/1998 | Rudie et al. |
| 5,776,176 A | 7/1998 | Rudie |
| 5,785,706 A | 7/1998 | Bednarek |
| 5,788,692 A | 8/1998 | Campbell et al. |
| 5,800,482 A | 9/1998 | Pomeranz et al. |
| 5,800,494 A | 9/1998 | Campbell et al. |
| 5,837,001 A | 11/1998 | Mackey |
| 5,842,984 A | 12/1998 | Avitall |
| 5,849,028 A | 12/1998 | Chen et al. |
| 5,863,291 A | 1/1999 | Schaer |
| 5,885,278 A | 3/1999 | Fleischman |
| 5,957,969 A | 9/1999 | Warner et al. |
| 5,971,983 A | 10/1999 | Lesh |
| 6,014,579 A | 1/2000 | Pomeranz et al. |
| 6,032,077 A | 2/2000 | Pomeranz |
| 6,175,768 B1 | 1/2001 | Arndt et al. |
| 6,190,382 B1 | 2/2001 | Ormsby et al. |
| 6,230,060 B1 * | 5/2001 | Mawhinney ............... 607/101 |
| 6,383,182 B1 | 5/2002 | Berube et al. |
| 6,663,625 B1 | 12/2003 | Ormsby et al. |
| 7,004,938 B2 | 2/2006 | Ormsby et al. |
| 7,070,595 B2 | 7/2006 | Ormsby et al. |
| 7,322,959 B2 | 1/2008 | Warnack et al. |
| 2002/0091427 A1 | 7/2002 | Rappaport et al. |
| 2003/0100894 A1 | 5/2003 | Mahon et al. |
| 2004/0133254 A1* | 7/2004 | Sterzer et al. ............... 607/101 |
| 2005/0096647 A1 | 5/2005 | Steinke et al. |
| 2005/0165388 A1* | 7/2005 | Bhola ............... 606/14 |
| 2006/0142752 A1 | 6/2006 | Ormsby et al. |
| 2006/0235286 A1 | 10/2006 | Stone et al. |
| 2006/0287649 A1 | 12/2006 | Ormsby et al. |
| 2007/0066972 A1* | 3/2007 | Ormsby et al. ............... 606/41 |
| 2008/0015570 A1 | 1/2008 | Ormsby et al. |

FOREIGN PATENT DOCUMENTS

| | | |
|---|---|---|
| WO | 97/26544 A1 | 7/1997 |
| WO | 98/49933 | 11/1998 |
| WO | 02/26146 | 4/2002 |

OTHER PUBLICATIONS

European Communication dated Sep. 30, 2011 and Supplementary European Search Report dated Sep. 21, 2011 for EP 09774339.7.

Written Opinion and Search Report dated Feb. 2, 2010 in PCT Application No. PCT/US2009/49251.

* cited by examiner

ANGIOPLASTY AND TISSUE ABLATION APPARATUS AND METHOD

BACKGROUND

1. Field of the Invention

The present invention generally relates to medical devices which are used for the irradiation of biological tissues, such as devices for the ablation of biological tissues, and more particularly to a combined angioplasty and tissue ablation apparatus.

2. Related Art

Angioplasty procedures, short for percutaneous transluminal coronary angioplasty ("PTCA") have been in extensive use in the United States since 1980 for the relief of angina (chest pain) and prevention of heart attacks. In angioplasty procedures, an inflatable balloon is inserted into a clogged artery and inflated at the clogged site to clear blockage, thus allowing the restoration of blood flow. Before angioplasty, bypass surgery was the only option for people with clogged arteries. In bypass surgery, doctors must open the patient's chest to reroute blood vessels to the heart. Angioplasty is less invasive, as the balloon is fed in through the blood vessels without the necessity of opening the chest of the patient. Thus, patient recovery time is generally faster with angioplasty, than with bypass surgery.

In common angioplasty procedures, a catheter threaded on a thin guidewire is passed into the blood vessel. The catheter, which is a tubular medical device, is about 3 ft (91 cm) long. The surgeon feeds the catheter through the blood vessels into the coronary artery. The catheter releases dye, so its precise position can be seen on a fluoroscope. When the first catheter is in place at the clogged arterial site, the surgeon feeds a smaller, balloon-tipped catheter through it. The length of the balloon is approximately equal to the length of the clogged or partially blocked region to be treated. The surgeon guides the balloon-tipped catheter into the narrowed artery until the balloon is aligned with the correct region, and the balloon is then inflated. Inflation of the balloon expands the artery, clears the arterial blockage and restores or otherwise improves the blood flow. After the procedure, the balloon is deflated and the catheter is withdrawn form the artery. At times, in connection with the angioplasty procedure, a stent is mounted in a collapsed configuration over the balloon on the catheter and introduced into the blood vessel. Mounted on the inflating balloon, the stent expands as the balloon is inflated at the clogged arterial site, locks in place and forms a scaffold to hold the artery open.

The common observation in angioplasty is that up to half of all patients who undergo the procedure could experience restenosis—the re-narrowing of a coronary artery—or the formation of new blockages at the site of the angioplasty due to thrombosis, or blood clotting, or tissue growth at the site of treatment. While blood clot might be prevented or controlled by anti-clotting drugs, tissue growth, which is a proliferation of the "endothelial" cells, would tend to occur during the first 3 to 6 months after the procedure, and is not prevented by anti-clotting drugs. Accordingly angioplasty with or without stenting could eventually require a repeat procedure.

Various attempts have been made to address scar tissue build-ups. One approach is to apply energy to the clogged or restricted arterial site via tissue ablation with the objective of changing the properties of the biological tissues so as to reduce or present restenosis. Tissue ablation may employ different energy exchange modes, for example heat conduction and irradiation and means, such as radiofrequency, ultrasound, laser, cryogenic, and the like.

Within the radio frequency (RF) range, certain microwave ablation systems are used to destroy or ablate biological tissues. In one application, a microwave ablation system is used to ablate cardiac tissues that cause irregular heartbeats or arrhythmia, avoiding the need for more risky and invasive open heart surgery. In such an application, an ablation member such as an RF antenna is incorporated as part of a catheter, which can be deployed within the body vessel.

SUMMARY

The present invention combines an angioplasty balloon with a tissue ablation catheter apparatus. The embodiments described herein provide a RF transmission line with an RF antenna mounted at the distal end portion of the device along with a balloon in fluid communication with a fluid supply path through the catheter.

In one embodiment, an angioplasty and tissue ablation apparatus comprises a catheter which is inserted into a body vessel of a patient. The catheter has a proximal portion, a distal portion with an distal opening, and a lumen extending from the proximal portion to the distal portion for receiving a fluid. A radio-frequency ("RF") antenna mounted on the catheter, which receives and transmits radio-frequency energy for ablating the biological tissues of the body vessel. A balloon is sealingly mounted on the distal portion of the catheter around the RF antenna. The balloon has an exterior surface, and an interior volume in fluid communication with the lumen.

In one embodiment, the catheter incorporates a coaxial cable device comprising an inner conductive member and an outer conductive member associated with the RF antenna, which may be a helical coil antenna, a monopole antenna, or the like. In one embodiment, a dielectric medium is selectively disposed between the inner and outer conductors. The dielectric medium may comprise a solid or a fluid material, or a combination of both, and may assume alternative structure features. In lieu of a dielectric, a vacuum can be drawn between the inner and outer conductors, which may also serve to provide dielectric properties.

Once the tip or distal end portion of the catheter which carries the antenna and angioplasty balloon is positioned in a body vessel at the location of a narrowing of the vessel, the balloon is inflated to expand the vessel wall. RF energy is then applied to the expanded arterial wall, heating the tissue to fix the tissue in the expanded condition, making it less likely to re-grow. The balloon is then collapsed and the apparatus is removed from the vessel. In an alternative embodiment, the catheter may also be used for stent deployment in the narrowed vessel region. In this embodiment, an expandable stent is located on the collapsed balloon. Both the balloon and stent are expanded at a region to be treated, and the expanded stent remains in position in the expanded region of the vessel when the balloon is subsequently deflated.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

Certain embodiments as disclosed herein provide for a combined angioplasty and tissue ablation apparatus, which incorporates a catheter having a distal portion on which an radio frequency (RF) antenna is mounted for transmitting radio frequency (RF) energy, e.g. particularly in microwave frequency range, for the ablation of biological tissues, along with an angioplasty balloon.

After reading this description, it will become apparent to one skilled in the art how to implement the invention in various alternative embodiments and alternative applications. However, although various embodiments of the present invention will be described herein, it is understood that these embodiments are presented by way of example only and not limitation. As such, this detailed description of various alternative embodiments should not be construed to limit the scope or breadth of the present invention as set forth in the appended claims.

Figure 1:
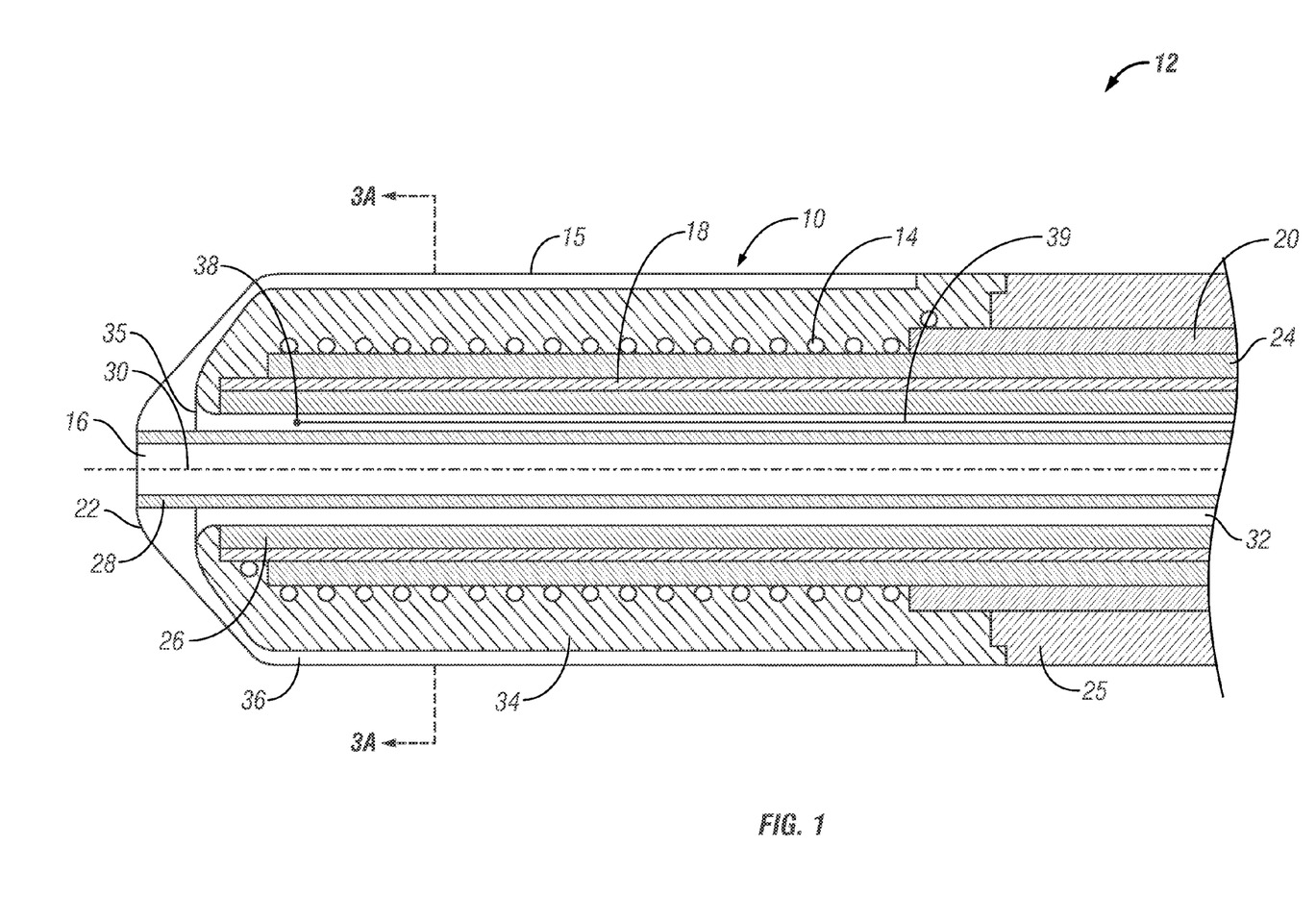
FIG. 1 is a cross-sectional view of the distal end portion of one embodiment of a combined angioplasty and tissue ablation catheter apparatus, with the angioplasty balloon in a deflated condition.
Figure 2:
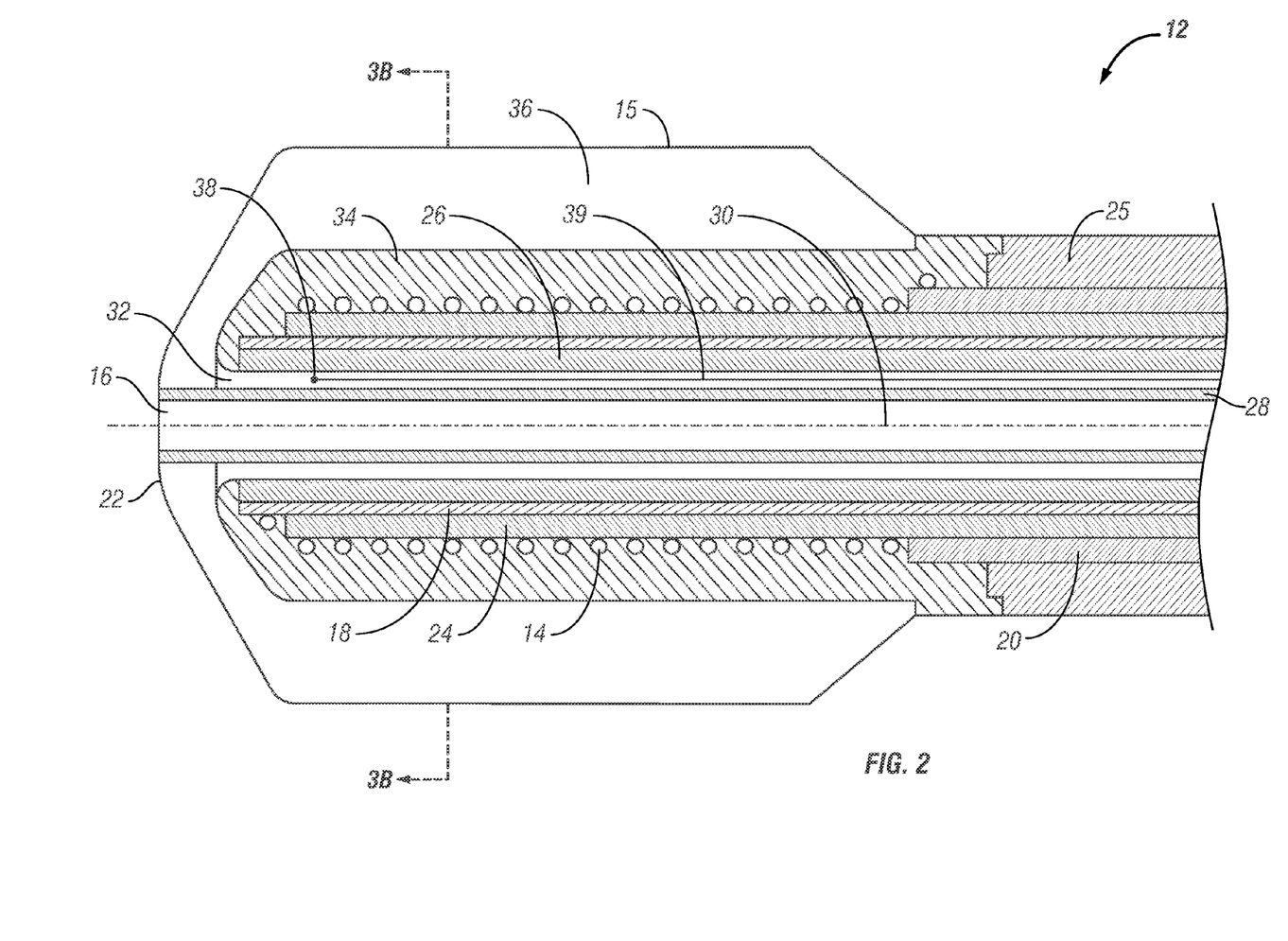
FIG. 2 is a cross-sectional view similar to FIG. 1, with the angioplasty balloon in an expanded condition.
Figure 3A:
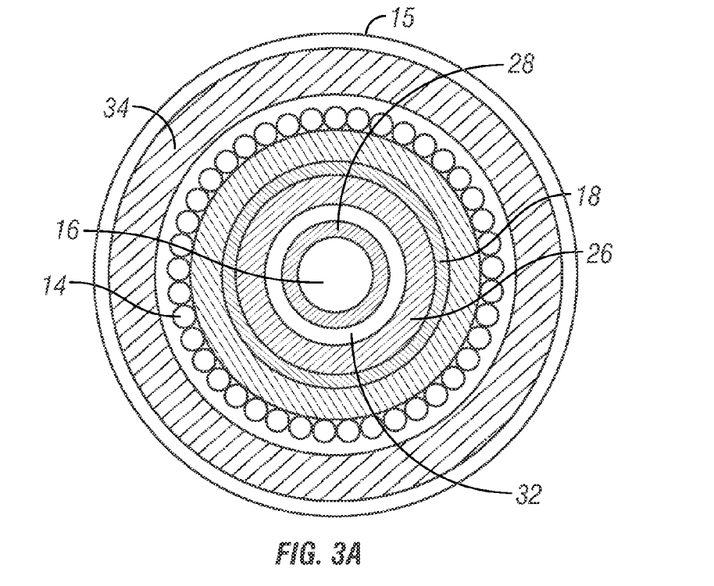
FIG. 3A is a sectional view on the lines 3A-3A of FIG. 1.
Figure 3B:
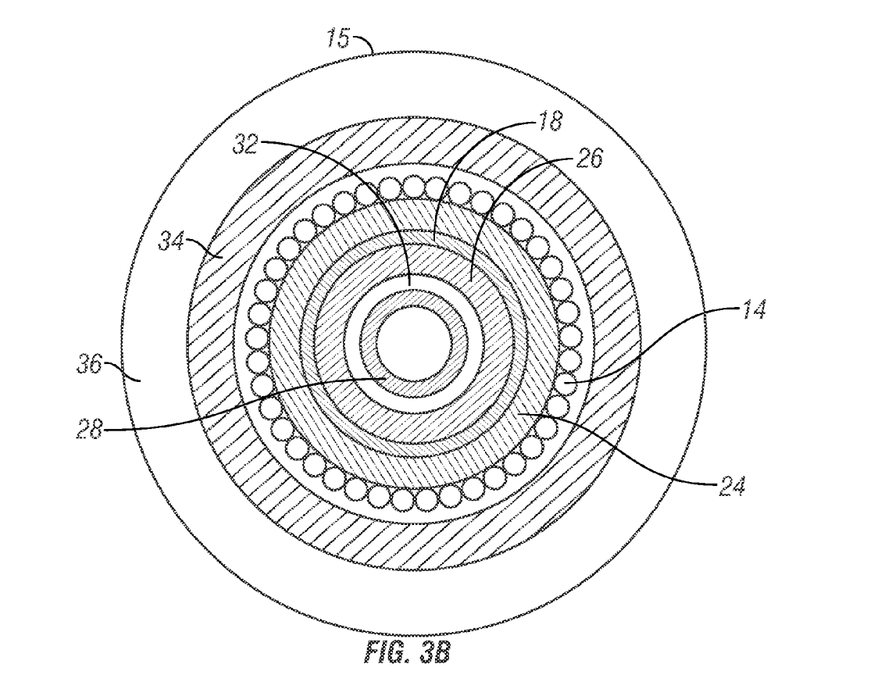
FIG. 3B is a sectional view on the lines 3B-3B of FIG. 2.

FIGS. 1 to 3 illustrate the distal portion 10 of a first embodiment of a combined angioplasty and tissue ablation apparatus 12. The distal portion 10 incorporates an ablation device 14, such as an RF antenna, for delivering electromagnetic energy to the treatment site, as well as an angioplasty balloon 15. The apparatus generally comprises a coaxial cable device similar to that described in co-pending application Ser. No. 11/781,467 filed on Jul. 23, 2007 and Ser. No. 11/858,736 filed on Sep. 20, 2007, the contents of both of which are incorporated herein by reference.

The length and diameters of the apparatus 12 are adapted as required to suit the particular medical procedure, as is known in the medical art. Apparatus 12 is generally tubular and has a multi-layer construction with a central bore or guidewire lumen 16 extending along its length from a proximal portion (not illustrated) to distal portion 10. Inner and outer electrically conductive tubular members or conductors 18, 20 extend coaxially from the proximal portion of the apparatus, with the inner conductor 18 extending up to a location close to the distal end or tip 22 of the apparatus, and the outer conductor 20 extending along the majority of the length of the apparatus but terminating at the distal end portion 10. An RF transmission waveguide is defined between the inner and outer conductors.

Inner conductor 18 and outer conductor 20 each comprise an elongated electrically conductive tubular member, with outer conductor 20 arranged in a substantially coaxial relationship over at least a portion of length of the inner conductor 18. This arrangement defines an annular space between the walls of the inner and outer conductors where a dielectric medium 24 is placed. The dielectric medium may be a solid or a fluid or a combination of solid and fluid which fills the space between the inner outer conductor. Any unfilled space may be evacuated to form a vacuum or filled with an alternative dielectric solid or fluid material. A dielectric fluid medium such as air may be dispensed in lieu of a solid dielectric layer. Vacuum, which also exhibits dielectric property, may be introduced by the evacuation of air and sealing the space between the distal and proximal end portions of the cable during manufacture. Alternately, a vacuum source may be configured in fluid communication with the space between the inner and outer conductors.

An outer jacket or casing 25 of dielectric polymer material encloses the co-axial conductors and extends to the distal portion 10 of the apparatus. An inner liner or support tube 26 of flexible dielectric material extends within the inner conductor 18 up to a location close to the distal end or tip of the apparatus. A guide tube or guide member 28 extends coaxially within tube 26 up to the distal tip of the device and defines the guide passageway or lumen 16 for guide wire 30 which projects forward from the coaxial cable device out through the open end of tube 28. The annular space 32 between coaxial tubes 26 and 28 defines a passageway for filling and extracting of fluid, such as saline, to expand and collapse balloon 15, as discussed in more detail below. As illustrated in FIG. 1 and 2, guide tube 28 projects forward from the open distal end 35 of annular space or passageway 32.

Figure 7:
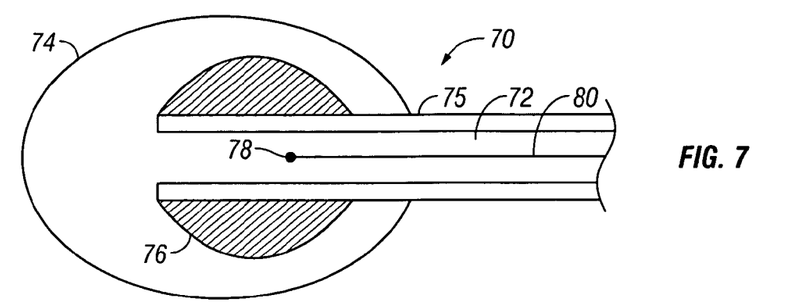
FIG. 7 is a schematically simplified view of the distal end portion of another embodiment of a combined angioplasty and tissue ablation apparatus, with the balloon expanded.
Figure 8:
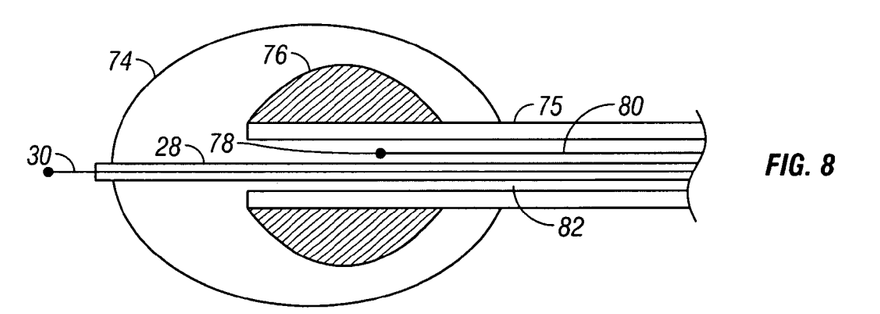
FIG. 8 is a schematically simplified view of the distal end portion of another embodiment of a combined angioplasty and tissue ablation apparatus, with the balloon expanded.

In this embodiment, the ablation device 14 located at the distal portion 10 of the apparatus comprises a helical coil radio frequency (RF) antenna, which is electrically coupled to both the outer coaxial conductor 20 and to the inner conductor 18 at its opposite ends. The antenna is adapted to receive and radiate electromagnetic energy from a source of radio frequency energy coupled with the inner and outer coaxial conductors. The helical coil antenna 14 is coated with an outer coating layer 34 of dielectric material such as a polymeric dielectric encapsulant which protects the structural integrity of the coil and also shields it from the surrounding biological environment. In alternative embodiments, other forms of ablation devices or radio frequency antennas may be used in place of the helical coil antenna 14, such as a monopole bead antenna as illustrated in the embodiments of FIGS. 7 and 8 described in more detail below, or a pair of spaced electrically conductive microstrips disposed at the distal end portion of the coaxial cable device, as described in U.S. Pat. No. 6,663,625, the contents of which are incorporated herein by reference. The RF antenna 14 includes an electrically conductive material or wire strip that is wound in a helical fashion to form the helical coil. The appropriate diameter, pitch and length of the coil winding and the selection of the conductive material or wire strip are a matter of choice, which can vary according to the particular procedure requirements as known in the art. Thus these design elements and considerations are not detailed here.

Balloon 15 has a proximal end secured to the outer casing 25 and a distal end bonded to the tip of inner guide tube 28, so that the internal volume 36 of the balloon is in communication with the fluid filling/extraction passageway 32 at the open forward end 35 of the passageway. In this embodiment, a temperature sensor 38 is located in passageway 32 at the distal end portion 10 of the apparatus so as to detect the temperature in the vicinity of the tissue ablating end of the apparatus, and electrical leads 39 extend through the passageway 32 along the length of apparatus 10 for suitable connection to monitoring devices or the like. In one embodiment, RF energy delivered to the targeted biological tissue may be varied in response to the detected reflected power (reverse power) to the antenna and the detected tissue temperature, as described in more detail in co-pending application Ser. No. 11/479,259, the contents of which are incorporated herein by reference in their entirety. Alternatively, the tissue temperature may be monitored and the ablation procedure ended when a predetermined temperature is reached. In some applications, electrocardiogram (EKG) electrodes may also be incorporated in the distal end portion of the cable apparatus.

FIGS. 2 and 3B illustrate the distal portion 10 of the apparatus with the balloon 15 in an expanded condition. Fluid such as saline solution is injected into the balloon through passageway or lumen 32, which pressurizes the balloon and inflates the balloon 15. The RF antenna is then energized to effect tissue ablation. Once a procedure is complete, the balloon is collapsed or deflated by extracting the fluid from the balloon via the same passageway.

Figure 4:
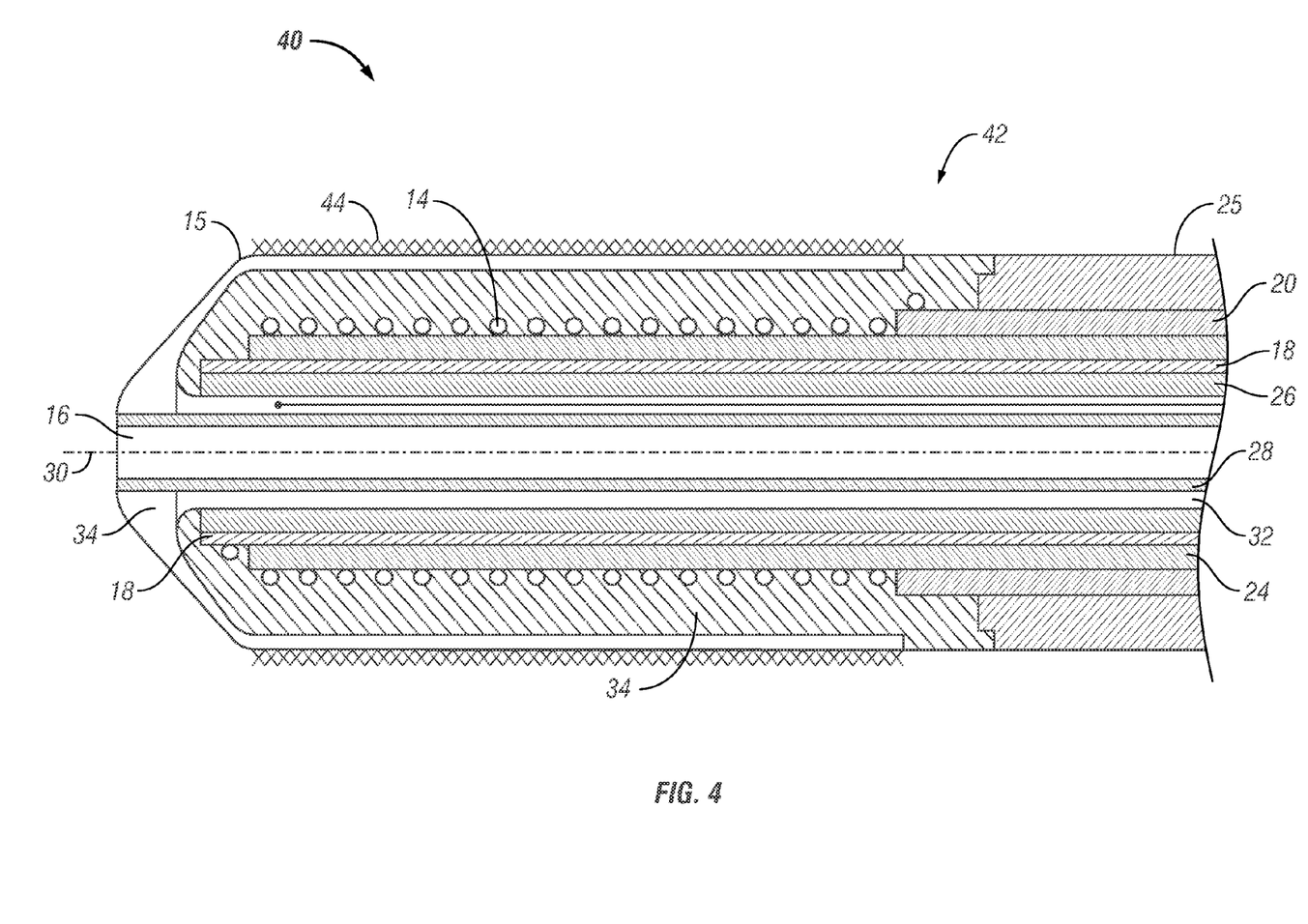
FIG. 4 is a cross-sectional view of the distal end portion of another embodiment of a combined angioplasty and tissue ablation catheter apparatus, with the angioplasty balloon in a deflated condition and carrying a non-expanded stent.
Figure 5:
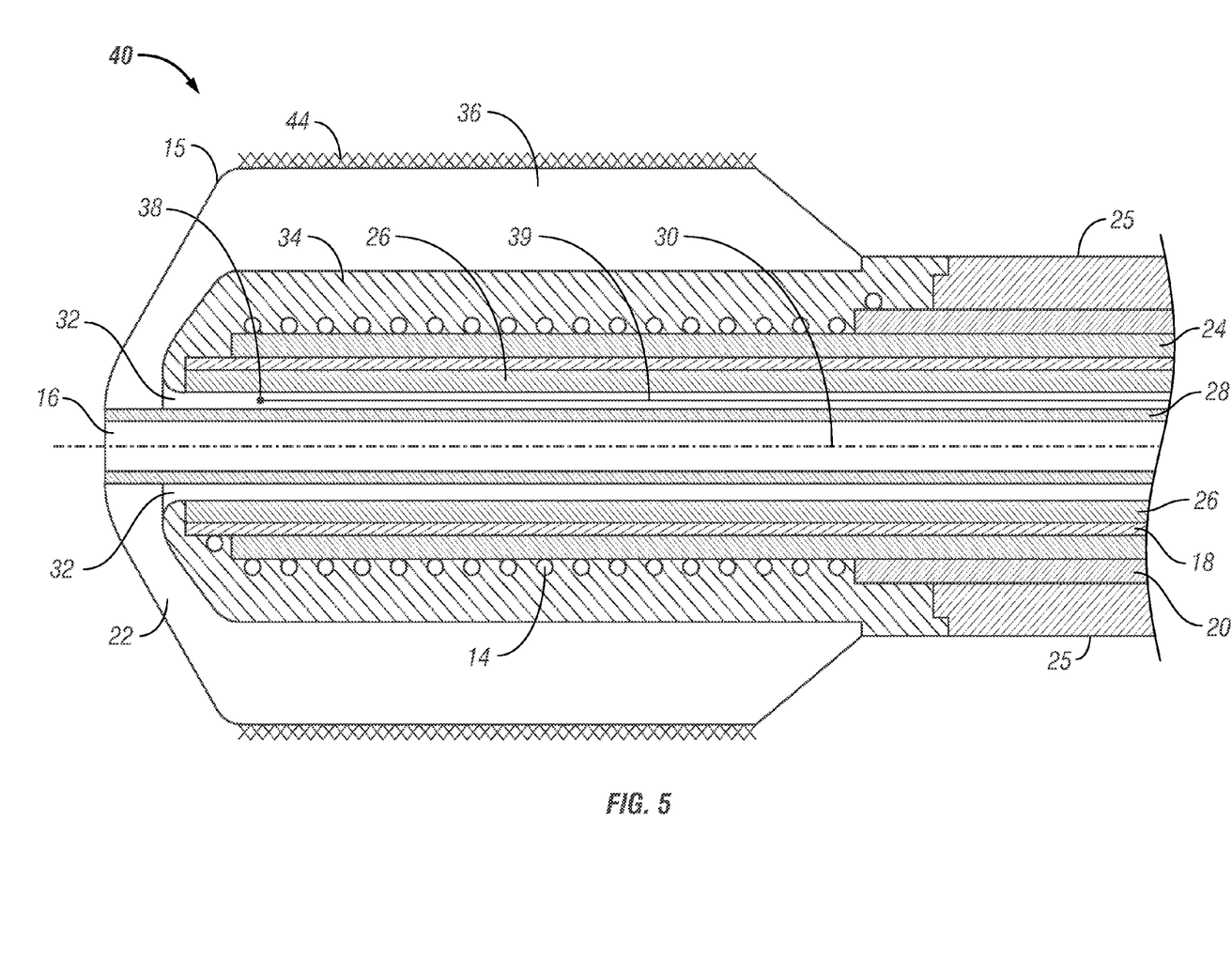
FIG. 5 is a cross-sectional view similar to FIG. 1, with the angioplasty balloon and stent in an expanded condition.

FIGS. 4 and 5 illustrate a modified apparatus 40 in which the distal tip portion 42 has an expandable stent 44 loaded over balloon 15, as indicated. The apparatus 40 of FIGS. 4 and 5 is otherwise identical to that of FIGS. 1 to 3, and like reference numbers are used for like parts as appropriate.

Figure 6A:
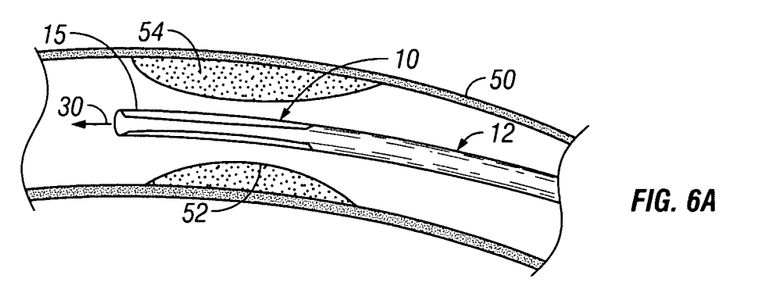
FIG. 6A is a schematic view illustrating positioning of the apparatus of FIGS. 1 to 3 at a region in a body vessel which is to be treated by angioplasty and application of RF radiation.

FIGS. 6A to 6D illustrate several steps in a medical procedure using the combined angioplasty and tissue ablation apparatus as described above in connection with FIGS. 1 to 3. FIG. 6A illustrates the distal portion 10 of the apparatus deployed in a body vessel 50 at the location of a partial clog or narrowing 52 of the vessel. The balloon is still in a collapsed condition in FIG. 6A, allowing the tip of the apparatus to be readily maneuvered through the body vessel to a site of interest. In this embodiment, the apparatus is threaded on guide wire 30 into the vessel, but the guide wire 30 may be eliminated in alternative embodiments. Dye may be released by the catheter or apparatus 10 so that the precise position of the tip can be seen on a fluoroscope, or other positioning means may be used to locate the distal end portion 10 within the narrowed region 52 of the vessel.

Figure 6B:
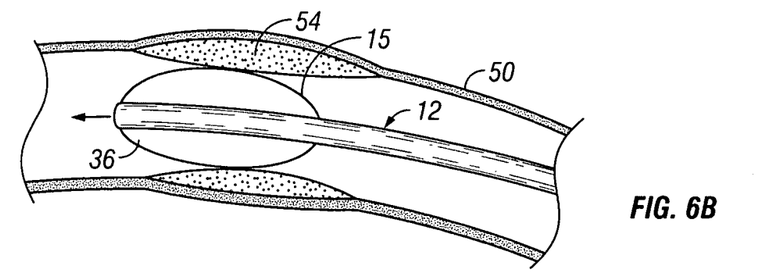
FIG. 6B is a schematic view similar to FIG. 6A illustrating expansion of the balloon in the vessel.

Once the distal portion is properly positioned, fluid is supplied through passageway 32 to the inside of balloon 15, so that the balloon expands into an expanded condition, as illustrated in FIG. 6B. The expanding balloon pushes the surrounding tissue or plaque material 54 thereby urging the blockage outwardly against the vessel walls and expanding the vessel diameter. The expanded tissues or plaques are then heated by actuating the antenna to direct RF energy into the tissues surrounding the end portion 10 of the apparatus, coagulating and ablating the tissues, so that they tend to be fixed in the expanded condition as illustrated.

The RF antenna imparts substantially uniformly distributed electromagnetic field energy transmitted by the helical coil. The power of the electromagnetic field transmitted is substantially normal to the longitudinal axis of the RF antenna. The energy delivered for the ablation is substantially uniformly distributed along the antenna, which is independent of the contact between the antenna and the tissue to be ablated.

Figure 6C:
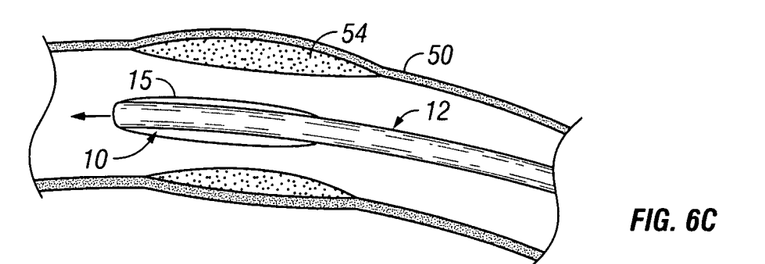
FIG. 6C is a schematic view similar to FIGS. 6A and 6B illustrating collapsing of the balloon after angioplasty and ablation is complete.
Figure 6D:
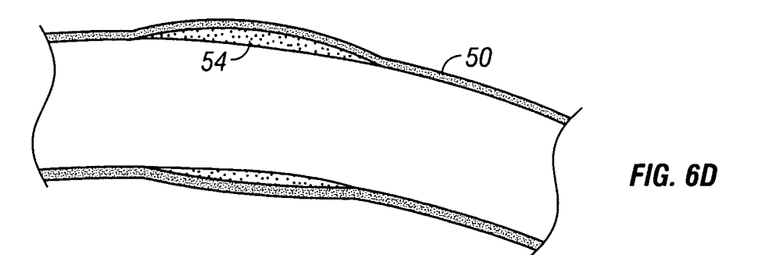
FIG. 6D is a schematic view similar to FIG. 6C illustrating the treated region after retraction of the catheter apparatus from the vessel.

When the balloon is expanded and RF energy has been applied to the expanded surrounding tissue for a desired length of time, the RF power supply is switched off, and fluid is extracted from the interior 36 of the balloon 15 via passageway 32. As a result, the balloon deflates back to the original position, as seen in FIG. 6C. At the same time, the surrounding tissue at the treatment site remains fixed in the expanded condition, opening the vessel and allowing blood to flow. The apparatus is then retracted from the body vessel (FIG. 6D).

The same procedure is carried out with the apparatus of FIGS. 4 and 5. In this embodiment, when the balloon is deflated after treatment is complete, the stent 44 remains in the expanded condition and helps to hold open the previously narrowed area of the vessel. As is known in the field, stent 44 may be a drug releasing stent which releases a drug to resist re-stenosis of plaque over the stent.

FIG. 7 is a simplified view of the distal end portion 70 of another embodiment of a combined angioplasty and tissue ablation apparatus. The multiple layers of the apparatus which were shown in FIGS. 1 to 4 are omitted in FIG. 7 for simplicity, but may be the same as illustrated in FIGS. 1 to 4. One difference in this embodiment is that the guide wire 30 and guide wire tube 28 of the preceding embodiments is eliminated, leaving a single central lumen or passageway 72 which is open at its distal end. A balloon 74 is secured to the outer casing 75 at the distal end portion 70 of the apparatus and extends over the open forward end of passageway 72. Fluid is supplied to the interior of balloon 74 through the open forward end of passageway 72.

In the embodiment of FIG. 7, the helical coil antenna 14 of the previous embodiments is replaced with a monopole antenna 76 which is surrounded by balloon 74, although a helical coil antenna may be used in alternative embodiments. As in the previous embodiments, a temperature sensor 78 is provided at the distal end portion 70 of the device, with temperature sensor wires 80 extending from sensor 78 to the proximal end portion.

FIG. 8 illustrates a modification of the embodiment of FIG. 7 which includes a guide wire 30 extending through an inner guide tube 28 which extends coaxially through the device, as in the first embodiment, with the temperature sensor 78 located in the outer annular passageway 82 of lumen 72 outside guide tube 28. This embodiment is otherwise identical to that of FIG. 7, and like reference numerals have been used for like parts as appropriate.

In FIGS. 7 and 8, the balloon 74 is shown in an expanded condition after fluid has been supplied to the interior of balloon 74 via passageway 72 in FIG. 7, and via outer annular passageway 82 in FIG. 8. In either case, fluid is extracted along the same passageway when treatment is complete, and the procedure is identical to that described above in connection with FIGS. 6A to 6D. As in FIGS. 4 and 5, an expandable stent 44 may be loaded on balloon 74, and the device may be used to position the stent in the expanded tissue, with the stent remaining in position after the balloon is deflated.

Figure 9:
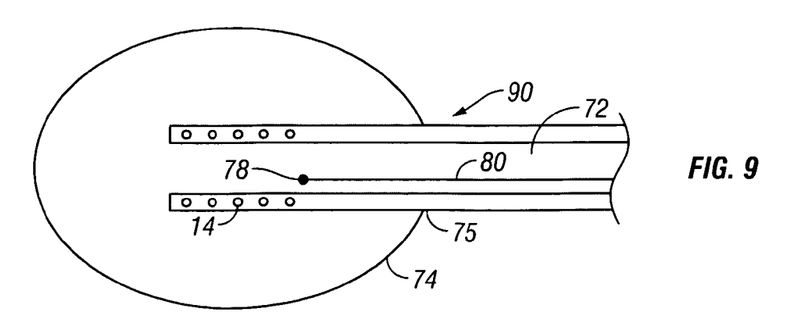
FIG. 9 is a schematically simplified view similar to FIGS. 7 and 8 of the distal end portion of another embodiment of a combined angioplasty and tissue ablation apparatus.

FIG. 9 illustrates another embodiment of a combined angioplasty and tissue ablation device 90. This device is identical to that of FIG. 7 except that the monopole antenna 76 is replaced by a helical coil antenna 14 as in FIGS. 1 to 3, and like reference numbers are used for like parts as appropriate.

The outer dimensions of the body of the coaxial cable apparatus in each of the above embodiments may be adapted as required to suit the particular medical procedure, as is well known in the medical art. The device is used to expand tissue such as plaque in narrowed regions of body vessels, and subsequently to heat the expanded tissue in order to fix it in the expanded condition. As described in connection with FIGS. 4 and 5, the device may also be used to implant a stent in the expanded tissue region.

In each of the above embodiments, the ablation apparatus has an RF antenna and an angioplasty balloon mounted at its distal end portion, and may also have an expandable stent loaded over the balloon. The RF antenna is adapted to receive and radiate electromagnetic energy in order to treat a selected biological tissue site after expansion with the inflated balloon, by changing a property of the biological tissue at the site. An example of a suitable spectrum of radio frequency energy for use in tissue ablation is that of the microwave frequency range above 300 MHz. The RF antenna is capable of applying substantially uniformly distributed electromagnetic field energy along the RF antenna in a direction substantially normal to the longitudinal axis of the antenna. The elongated, flexible coaxial cable apparatus is connected to an RF source and a supply of fluid such as saline to inflate the balloon. In alternative embodiments, a suitable shaping or steering mechanism within the central lumen may also be included for controlling the shape or deflection of the distal end portion of the coaxial cable device on which the RF antenna and balloon are located, as described in U.S. Pat. No. 7,004,938, the contents of which are incorporated herein by reference.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are, therefore, representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

The invention claimed is:

1. An angioplasty and tissue ablation apparatus comprising:
  a catheter adapted for insertion into a body vessel of a patient, the catheter having a proximal end, a proximal portion extending from the proximal end, a distal portion having a distal end, and a lumen between the proximal portion and the distal end for receiving a fluid;
  a radio-frequency ("RF") antenna mounted on the distal portion of the catheter and spaced radially outward from the lumen, the RF antenna having a proximal end and a distal end, the RF antenna adapted to receive and generate radio-frequency energy for ablating the biological tissues of the body vessel;
  an RF transmission line which extends from the proximal portion of the catheter to the RF antenna and which transmits RF energy from the proximal portion to the RF antenna;
  a guide tube extending through the lumen and spaced radially inwardly from the RF antenna, the guide tube defining an annular passageway in the lumen outside the guide tube, the annular passageway having an open distal end spaced forward from the proximal end of the antenna;
  the guide tube having a distal end portion projecting forward from the open distal end of the passageway and the distal end of the catheter;
  a guide wire extending through the guide tube; and
  a balloon having a distal end sealingly mounted on the projecting distal end portion of the guide tube at a location spaced forward from the distal end of the catheter and a proximal end sealingly mounted on the distal end portion of the catheter adjacent the proximal end of the antenna, whereby the RF antenna is inside the balloon and the interior of the balloon is in communication with the annular passageway, the annular passageway comprising a fluid injection and extraction path through which fluid is supplied to inflate the balloon and fluid is extracted to collapse the balloon.

2. The apparatus of claim 1, wherein the radio-frequency transmission line comprises a hollow coaxial electrical cable having an inner conductor comprising a first elongated electrically conductive tubular member, an outer conductor comprising a second elongated electrically conductive tubular member disposed in a substantially coaxial relationship over at least a portion of the inner conductor and defining a space between the walls of the inner conductor and the outer conductor, and a dielectric interposed in the space.

3. The apparatus of claim 2, wherein the outer conductor has a distal end adjacent the proximal end of the balloon, the inner conductor and dielectric have a distal end portion projecting beyond the distal end of the outer conductor, and the RF antenna comprises a helical coil mounted over the distal end portion of the dielectric and inner conductor.

4. The apparatus of claim 1, wherein the RF antenna is adapted to operate at a frequency greater than 300 Megahertz (MHz) of the electromagnetic spectrum.

5. The apparatus of claim 1, wherein the RF antenna comprises a monopole.

6. The apparatus of claim 1, further comprising an expandable stent removably mounted over the balloon, the stent being adaptable for installation in the body vessel on expansion of the balloon.

7. The apparatus of claim 1, further comprising
  a temperature sensor located in the lumen at the distal portion of the catheter, the temperature sensor being spaced inwardly from the RF antenna and balloon.

8. The apparatus of claim 7, wherein the temperature sensor is located in the annular passageway.

9. The apparatus of claim 1, further comprising an expandable stent removably mounted over the balloon.

10. An angioplasty and tissue ablation apparatus comprising:
  a catheter adapted for insertion into a body vessel of a patient, the catheter having a proximal end, a proximal portion extending from the proximal end, and a distal portion having a distal end;
  the catheter comprising a radio frequency (RF) transmission line and an outer casing enclosing the RF transmission line, the RF transmission line comprising a hollow coaxial electrical cable having a proximal portion and a distal portion;
  the hollow coaxial electrical cable comprising an inner conductor and an outer conductor each comprising an elongated electrically conductive tubular member, the outer conductor disposed in a substantially coaxial relationship over at least a portion of the inner conductor to define an annular space between the inner conductor and the outer conductor, and a dielectric filling the annular space between the inner and outer conductor;

the inner conductor having a distal end portion extending beyond a distal end of the outer conductor;

the cable defining a lumen extending inside the inner conductor and having an open distal end;

a balloon sealingly mounted on the distal portion of the catheter and extending from the distal end of the outer conductor over the distal end portion of the inner conductor and the distal end of the catheter, the balloon having an exterior surface, an interior surface, and an interior volume in fluid communication with the lumen; and a radio frequency (RF) ablation antenna disposed substantially within the interior volume of the balloon and spaced inwardly from the interior surface of the balloon, the RF antenna adapted to receive input RF energy from the transmission line and to transmit RF energy for the ablation of tissue at the biological vessel site.

11. The apparatus of claim 10, wherein the RF transmission line is adapted to transmit radio-frequency energy at a frequency greater than 300 Megahertz (MHz) of the electromagnetic spectrum.

12. The apparatus of claim 10, wherein the radio-frequency antenna comprises a helical coil circumscribing the distal end portion of the inner conductor.

13. The apparatus of claim 10, wherein the radio-frequency antenna comprises a monopole circumscribing the distal end portion of the inner conductor.

14. The apparatus of claim 10, which further comprises at least one temperature sensor disposed within the lumen.

15. The apparatus of claim 10, which further comprises an expandable stent removably mounted over the balloon.

16. An angioplasty and tissue ablation apparatus comprising:

a catheter adapted for insertion into a body vessel of a patient, the catheter having a proximal portion, a distal portion, and a distal end, and a lumen between the proximal portion and the distal end for receiving a fluid;

a radio-frequency ("RF") antenna mounted on the distal portion of the catheter, the RF antenna having a proximal end and a distal end and adapted to receive and generate radio-frequency energy for ablating the biological tissues of the body vessel;

a balloon sealingly mounted on the distal portion of the catheter to extend over the RF antenna and having an interior volume in fluid communication with the lumen, the balloon having a proximal end adjacent the proximal end of the RF antenna and a distal end spaced forward from the distal end of the antenna and the distal end of the catheter, the RF antenna extending over at least a major portion of the length of the balloon from the proximal end of the balloon; and a guide member extending through the lumen and having a distal end projecting forward from the distal end of the catheter, the distal end of the balloon being sealingly mounted on the projecting forward end of the guide member.

\* \* \* \* \*